US006506833B2

(12) United States Patent
Brungs et al.

(10) Patent No.: US 6,506,833 B2
(45) Date of Patent: Jan. 14, 2003

(54) FLUID THICKENERS COMPRISING NEUTRALIZED CROSSLINKED POLYMERS OF ACRYLAMIDOALKYLSULONIC ACIDS AND N-VINYLAMIDES

(75) Inventors: Peter Brungs, Altötting (DE); Mattias Löffler, Niedernhausen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/027,043

(22) Filed: Dec. 20, 2001

(65) Prior Publication Data

US 2002/0082373 A1 Jun. 27, 2002

Related U.S. Application Data

(62) Division of application No. 09/501,904, filed on Feb. 10, 2000, now Pat. No. 6,355,752.

(30) Foreign Application Priority Data

Feb. 11, 1999 (DE) ........................................ 199 05 639

(51) Int. Cl.[7] ............................ C08K 5/06; C08K 5/05
(52) U.S. Cl. ..................... 524/765; 424/78.03; 524/755
(58) Field of Search ................................. 524/755, 765

(56) References Cited

U.S. PATENT DOCUMENTS

| | | | |
|---|---|---|---|
| 4,471,097 A | | 9/1984 | Uhl et al. |
| 4,585,845 A | | 4/1986 | Engelhardt et al. |
| 4,624,795 A | | 11/1986 | Dawson et al. |
| 6,090,899 A | | 7/2000 | Futami et al. |
| 6,120,780 A | | 9/2000 | Dupuis et al. |
| 6,376,072 B1 | * | 4/2002 | Evans |

FOREIGN PATENT DOCUMENTS

| | | |
|---|---|---|
| EP | 0 510 246 | 10/1992 |
| EP | 0 816 403 | 1/1998 |
| EP | 0 936 228 | 8/1999 |
| WO | 98/00094 | 1/1998 |

OTHER PUBLICATIONS

EPO Search Report for application No. 00101919, mail date May 24, 2000.

Derwent Patent Family Abstract for EP 0816403, Jan. 7, 1998.

Derwent Patent Family Abstract for for EP 0936228, Aug. 18, 1999.

U.S. Ser. No. 09/501,904, filed Feb. 10, 2000, Peter Brungs, et al.

* cited by examiner

*Primary Examiner*—Christopher Henderson
(74) *Attorney, Agent, or Firm*—Richard P. Silverman

(57) ABSTRACT

Water-soluble or water-swellable polymers, preferably having a particle size no greater than 10 $\mu$m, which, in addition to from 0.01 to 5% by weight of crosslinking structures originating from monomers having at least two olefinic double bonds, comprise, in random distribution, from 1 to 50% by weight of the repeat structural unit (1) and from 49.99 to 98.99% by weight of the repeat structural unit (2), $$-\!\!\left[CH_2-\underset{\underset{R^1-NCOR^2}{|}}{CH}\right]\!\!- \quad (1)$$

$$-\!\!\left[CH_2-\underset{\underset{CONHZSO_3NH_4}{|}}{CR^3}\right]\!\!- \quad (2)$$

in which $R^1$, $R^2$ and $R^3$ independently of one another are a hydrogen atom or a methyl group, and Z is a $C_1$–$C_4$-alkylene group.

These polymers are used as thickeners, preferably in cosmetic or pharmaceutical preparations.

7 Claims, No Drawings

FLUID THICKENERS COMPRISING NEUTRALIZED CROSSLINKED POLYMERS OF ACRYLAMIDOALKYLSULONIC ACIDS AND N-VINYLAMIDES

CROSS-REFERENCE TO RELATED APPLICATION

This application is a Division of application Ser. No. 09/501,904 filed Feb. 10, 2000, now U.S. Pat. No. 6,355,752 the contents of which is hereby incorporated by reference.

BACKGROUND OF THE INVENTION

The present invention relates to the preparation of water-soluble or water-swellable copolymers based on ammonium salts of acrylamidoalkylsulfonic acids and N-vinylcarboxamides, and to their use as thickeners, stabilizers of emulsions and dispersions, and as slip agents in cosmetic and pharmaceutical compositions for adjusting the viscosity of aqueous solutions.

DESCRIPTION OF THE RELATED ART

Multicomponent systems which contain water or solvent, such as solutions, emulsions or suspensions, are frequently adjusted to higher viscosities or thickened for reasons of cost or performance or for stability reasons.

Thus, for example, by increasing the viscosity of the external or internal phase of emulsions or suspensions, it is possible to significantly prolong the time before the components of such a system separate, which becomes apparent from an extension in the shelf life. For many products, increasing the viscosity also improves their ability to be distributed uniformly, in particular on uneven surfaces. This is true particularly for skincare compositions and pharmaceutical ointments on the skin. In the case of many industrial products, such as wallpaper stripping agents, paint strippers or aircraft de-icers, the increased viscosity prevents premature run-off from the surface to be treated. The more uniform distribution and extended contact time result in an increase in effectiveness. As well as the performance advantages mentioned, the high viscosity of such preparations also offers further advantages during preparation, packaging, containerizing and storage, as well as during transportation, the thickening of acidic media being of particular significance from a safety viewpoint.

In general, the rheological properties during the preparation and/or formulation of cosmetic, pharmaceutical or technical preparations are a decisive criterion for the use of these products in practice. Even when used in very small quantities, the thickeners employed should lead to adequate thickening. However, the color and principal properties of the medium to be thickened must not be changed.

A large number of different systems are given in the specialist literature for adjusting the rheological properties of aqueous or solvent-containing systems, emulsions, suspensions. Known examples are cellulose ethers and other cellulose derivatives (e.g. carboxymethylcellulose, hydroxyethylcellulose), gelatin, starch and starch derivatives, sodium alginate, fatty acid polyethylene glycol ester, agar agar, tragacanth or dextrin. The synthetic polymers used are a variety of materials, such as, for example, polyvinyl alcohols, polyacrylamides, polyacrylic acid and various salts of polyacrylic acid, polyvinylpyrrolidone, polyvinyl methyl ether, polyethylene oxides, copolymers of maleic anhydride and vinyl methyl ether, and various mixtures and copolymers of the compounds given above.

However, said compounds exhibit various disadvantages upon use. Thus, for example, the cellulose derivatives and, generally, the materials based on natural raw materials and the formulations resulting therefrom are very susceptible to bacteria. In applications, they are mostly noticeable by the formation of unpleasant "stringing" gels. Fatty acid polyethylene glycol esters tend toward hydrolysis in the presence of water and the insoluble fatty acids which form cause undesired clouding. Thickeners of natural origin (e.g. agar agar or tragacanth) have a greatly fluctuating composition, depending on their origin.

EP-A-0 816 403 and WO 98/00 094 describe crosslinked homopolymers of 2-acrylamido-2-methylpropanesulfonates and their use as thickeners.

EP-A-0 510 246 describes, inter alia, crosslinked copolymers of N-vinylcarboxamides and unsaturated alkylamides substituted by a sulfonate group, which are likewise suitable as thickeners. The sulfonic acid group here is exclusively in the form of the free acid or as alkali metal salt.

SUMMARY OF THE INVENTION

Surprisingly, we have now found that ammonium salts of various acrylamidoalkylsulfonic acids, in particular the ammonium salt of 2-acrylamido-2-methylpropanesulfonic acid, are sufficiently soluble in solvents which are acceptable for cosmetic applications, such as alcohols or alcohol mixtures, in particular in tert-butanol, and are therefore highly suitable for a copolymerization with N-vinylcarboxamides which are likewise soluble in these solvents or solvent mixtures, and as monomers which act as crosslinkers. In contrast to this, according to the prior art, it is obligatory to work in an aprotic solvent. Since the ammonium salt of 2-acrylamido-2-methylpropanesulfonic acid used for the polymerization is in ionic form, the crosslinked copolymer obtained no longer needs to be neutralized in an involved manner, but can be used as thickener immediately following polymerization and removal of the solvent. As a further advantage, the ratio of ionic to neutral building blocks can be controlled by virtue of the N-vinylcarboxamide incorporated as comonomer, thus enabling the thickening action and salt stability to be regulated and be better matched to specific requirements. The polymerization in alcohol or alcohol mixtures having a water content of less than 10% by weight and here in particular in tert-butanol furthermore gives products which, with regard to their residual content of solvent remaining in the product, are toxicologically acceptable and can therefore be used, for example, in cosmetic products.

DESCRIPTION OF THE PREFERRED EMBODIMENTS

The present invention provides water-soluble or water-swellable polymers, preferably having a particle size no greater than 10 μm and which, in addition to from 0.01 to 5% by weight of crosslinking structures originating from monomers having at least two olefinic double bonds, comprise, in random distribution, from 1 to 50% by weight of the repeat structural unit (1) and from 49.99 to 98.99% by weight of the repeat structural unit (2),

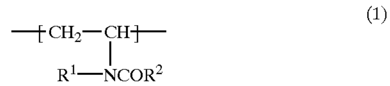

(1)

-continued

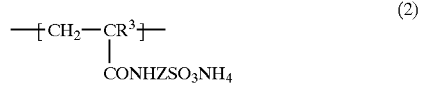

(2)

in which $R^1$, $R^2$ and $R^3$ independently of one another are a hydrogen atom or a methyl group, and Z is a $C_1$–$C_4$-alkylene group.

Preferred polymers according to the invention comprise from 2 to 30% by weight of structural units of the formula (1), preferably derived from N-vinylformamide, from 69.5 to 97.5% by weight of structural units of the formula (2), preferably derived from the ammonium salt of 2-acrylamido-2-methylpropanesulfonic acid and from 0.5 to 2% by weight of crosslinking structures originating from monomers having at least two olefinic double bonds.

Crosslinkable structures originating from monomers having at least two olefinic double bonds are preferably derived from, for example, dipropylene glycol diallyl ether, polyglycol diallyl ether, triethylene glycol divinyl ether, hydroquinone diallyl ether, tetraallyloxyethane or other allyl or vinyl ethers, polyfunctional alcohols, tetraethylene glycol diacrylate, triallylamine, trimethylolpropane diallyl ether, methylenebisacrylamide or divinylbenzene.

Particularly preferably, the crosslinking structures are derived from monomers of the formula (3),

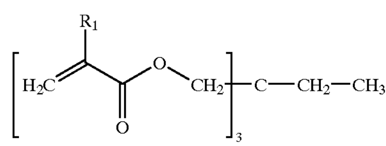

(3)

in which $R^1$ is hydrogen or methyl.

A preferred process for the preparation of the polymers according to the invention comprises, for the preparation of the polymers, a) dissolving or dispersing from 49.99 to 98.99 parts by weight, preferably from 69.5 to 97.5 parts by weight, in particular from 84.5 to 96.5 parts by weight, of the ammonium salt of acrylamidoalkylsulfonic acid of the formula (4),

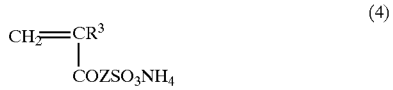

(4)

in which $R^3$ and Z are as defined above, in an alcoholic solvent or solvent mixture, or dissolving or dispersing from 49.99 to 98.99 parts by weight of the free acrylamidosulfonic acid derived from (4) in an alcoholic solvent or solvent mixture and converting the acid into the ammonium salt by introducing ammonia or ammoniacal solution, b) adding to the solution or dispersion obtained as in a) from 1 to 50 parts by weight, preferably from 2 to 30 parts by weight, in particular from 3 to 15 parts by weight, of the N-vinylcarboxamide of the formula (5)

$CH_2{=}CH_2$ | $R^1$—$NCOR^2$ (5)

in which $R^1$ and $R^2$ independently are as defined above, c) adding to the solution or dispersion obtained as in b) from 0.01 to 5 parts by weight, preferably from 0.5 to 2 parts by weight, of one or more crosslinkers having at least two double bonds, and d) starting the polymerization in a manner known per se using free-radical-forming compounds, and carrying out the polymerization at a temperature of from 10 to 150° C., the alcoholic solvent or solvent mixture used in a) being chosen such that the resulting polymers are largely insoluble in the solvent or solvent mixture.

The polymerization reaction is preferably carried out in a water-soluble alcohol or a mixture of two or more alcohols having from 1 to 4 carbon atoms, preferably in tert-butanol. The water content of the alcohol or of the mixture of two or more alcohols must not exceed 10% by weight, since lumps can otherwise appear during the course of polymerization. Specifically, the type and quantity of solvent is chosen such that the quantity of ammonium salt of acrylamidoalkylsulfonic acid, in particular of 2-acrylamido-2-methylpropanesulfonic acid, used or generated by introducing ammonia or ammoniacal solution is largely dissolved or dispersed. “Largely dissolved or dispersed” means that even after the stirrer has been switched off, solid material does not settle out of the solution or dispersion. The polymer formed in the course of the reaction should, by contrast, be largely insoluble in the chosen solvent (or solvent mixture). “Largely insoluble” here means that in the course of polymerization a readily stirrable pulpy polymer paste forms in which lumps or agglutination must not form. The filtrate which is obtainable by filtering the paste with suction must have a solids content of at most 5% by weight. If the polymers are soluble to a greater extent in the chosen solvent or solvent mixture, clumping can result during drying of the polymer paste.

The polymerization reaction itself is triggered in a manner known per se by free-radical-forming compounds, such as azo initiators (e.g. azobisisobutyronitrile), peroxides (e.g. dilauryl peroxide) or persulfates in a suitable temperature interval from 20° C. to 120° C., preferably between 40° C. and 80° C., and is continued over a period from 30 min to several hours.

The copolymer composition can be altered by varying the above-described feed ratio of the monomers, and the content of crosslinker and thus be used to achieve a tailored profile of properties. By incorporating more ammonium salts of acrylamidosulfonic acids, it is possible, for example, to improve the thickening action of the polymers, while by incorporating more % by weight of N-vinylcarboxamides, it is possible to improve the electrolyte compatibility of the polymers and their solubility in nonaqueous systems.

In contrast to polymers based on acrylic acid, which, in the neutral or slightly alkaline range in 1% strength aqueous solution, display viscosities of more than 30,000 mPa.s, but whose thickening ability (or the measured viscosity) deteriorates greatly with decreasing pH, the copolymers described according to the invention can maintain their viscosity (in 1% strength aqueous solution) up to an acidic pH of about 3.

EXAMPLES

Example 1

A 1000 ml flask fitted with anchor stirrer, reflux condenser, internal thermometer, feed option for $N_2$ and $NH_3$ was charged with 490.5 g of tert-butanol and 11.5 g of water. 80.75 g of 2-acrylamido-2-methylpropanesulfonic acid were then introduced and dispersed with vigorous stirring, clouding of the solvent being retained. Over a period of 30 min, 6.64 g of ammonia were introduced into the overhead gas space and the mixture was stirred for at least a further 30 min until a pH of 6–7 had been established. 4.25 g of N-vinylformamide and 1.45 g of trimethylolpropane triacrylate were added, and the receiver was flushed in each case with tert-butanol (about 6 ml) in order to minimize losses during the addition. The reaction mixture was then heated to a temperature of T=60° C., the reaction mixture being rendered inert by the simultaneous introduction of $N_2$. After the temperature of T=60° C. had been reached, 1.0 g of dilauryl peroxide was added. The reaction started immediately after the initiator had been added, recognizable from an increase in temperature and from flocculation of the polymer. Approximately 15 minutes after the polymerization reaction had started, the nitrogen feed was switched off. Approximately 30 min after the initiator dilauryl peroxide had been added the temperature reached a maximum (about 65–70° C.). For a further 30 min after this maximum had been passed, the mixture was heated to reflux and then stirred under these conditions for two hours.

The contents of the reaction vessel developed a pulp-like consistency over the course of the reaction, but could still be readily stirred. The mixture was then cooled to room temperature and the solid was filtered off with suction. The paste was dried at 60–70° C. in a vacuum drying cabinet for 24 h, giving 92.2 g of a fine white powder.

Example 2

Example 1 was repeated except that instead of trimethylolpropane triacrylate as crosslinker, 1.65 g of trimethylolpropane methacrylate were used.

Example 3

In accordance with Example 1, the crosslinked copolymer was prepared from 34 g of 2-acrylamido-2-methylpropanesulfonic acid, 51 g of N-vinylformamide and 1.9 g of trimethylolpropane triacrylate.

Example 4

In accordance with Example 1, the crosslinked copolymer was prepared from 76.5 g of 2-acrylamido-2-methylpropanesulfonic acid, 8.5 g of N-vinylformamide and 1.9 g of trimethylolpropane triacrylate.

Test Results

The powders obtained according to the examples were each dissolved in distilled water to 1.0% by weight, and the viscosity of the gels thereby formed was measured at 25° C. For this purpose, 5 g of dried polymer powder were in each case stirred into 495 g of distilled water in a 600 ml beaker, and the viscosity of the gel thereby formed was measured using an RVT Brookfield viscometer at 20 rpm. The gels prepared in this way are particularly suitable for cosmetic applications since they impart a pleasant feel to the skin when spread on the body.

The acid stability is likewise determined by measuring viscosity using the Brookfield viscometer. To this purpose, the copolymer prepared as in Preparation Example 1 was compared with a commercially available polymer based on acrylic acid (Carbopol® 934 from Goodrich). Using the method described above, 1.0% strength gels were prepared from the two polymers, their pH being adjusted to an acidic value (pH=about 3) and to a neutral value (pH=6–7)f, by adding NaOH or $H_3PO_4$ respectively as appropriate.

Table: Measured viscosities of the 1.0% strength gels.

| pH | Polymer from Example 1 | Carbopol 934 |
|---|---|---|
| 6–7 | 64,200 mPa · s | 76,600 mPa · s |
| about 3 | 50,200 mPa · s | 140 mPa · s |

As the table shows, in contrast to polymers based on acrylic acid, the polymers described according to the invention also exhibit very good thickening properties even at an acidic pH.

The copolymers according to the invention are notable for their good thickening action, in particular in cosmetic and pharmaceutical preparations at concentrations of solid copolymer of from 0.1 to 5 percent by weight, preferably from 0.5 to 2 percent by weight, particularly preferably from 0.7 to 1 percent by weight, based on the finished composition. At room temperature in deionized water, viscosities of more than 60,000 mPa.s are achieved at a pH of from 6 to 7.

The copolymers according to the invention exhibit only relatively slight changes in viscosity over a broad pH range, in particular in the range from pH 2.5 to 7. Furthermore, in the formulations they retain their good solubility in water and can be readily washed off from the skin. Their thickening and stabilizing properties are also effective in aqueous, alcoholic and/or glycol-containing solutions. They are UV stable and are stable over a wide temperature range from 0° C. to 50° C.

By varying the monomers acrylamidosulfonic acid ammonium salt and N-vinylcarboxamide, and the content of crosslinker, copolymers are obtained which can be used as thickeners both in oil-in-water emulsions, and in "water-in-oil" emulsions at a pH of from 7 to 2.5. Irrespective of whether the intention is to prepare lotions having a relatively low viscosity, or creams and ointments having high viscosities, emulsions comprise an oil substance consisting essentially of emulsifier/s and an oil phase in the amounts by weight of from 5 to 95%, preferably from 25 to 85%, and water up to 100% by weight. The oily substances used are vegetable, animal, mineral and synthetic oils, for example Guerbet alcohols having from 6 to 18, preferably from 8 to 10, carbon atoms, esters of linear $C_6$–$C_{13}$-fatty acids with linear $C_6$–$C_{20}$-fatty alcohols, esters of branched $C_6$–$C_{13}$-carboxylic acids with linear $C_6$–$C_{20}$-fatty alcohols, esters of linear $C_6$–$C_{18}$-fatty acids with branched alcohols, in particular 2-ethylhexanol, esters of linear and/or branched fatty acids with polyhydric alcohols (such as, for example, dimerdiol or trimerdiol) and/or Guerbet alcohols, triglycerides based on $C_6$–$C_{10}$-fatty acids, vegetable oils, branched primary alcohols, substituted cyclohexane, Guerbet carbonates, dialkyl ethers and/or aliphatic and aromatic hydrocarbons.

The emulsions can be in the form of skincare compositions, such as, for example, day creams, night creams, care creams, nourishing cream, body lotions, ointments and the like, and comprise, as further auxilaries and additives, coemulsifiers, superfatting agents, fats, waxes, stabilizers, biogenic active ingredients, glycerol, preservatives, pearlizing agents, dyes and fragrances.

Possible superfatting agents are substances such as, for example, polyethoxylated lanolin derivatives, lecithin derivatives, polyol fatty acid esters, monoglycerides and fatty acid alkanolamides, the latter also serving as foam stabilizers. Typical examples of fats are glycerides, and suitable waxes are, inter alia, beeswax, paraffin wax or microwaxes, optionally in combination with hydrophilic waxes, e.g. cetyl stearyl alcohols.

Stabilizers which can be used are metal salts of fatty acids, such as, for example, magnesium stearate, aluminum stearate and/or zinc stearate. Examples of biogenic active ingredients are plant extracts and vitamin complexes.

Suitable preservatives are, for example, phenoxyethanol, formaldehyde solution, parabens, pentanediol or sorbic acid.

Suitable pearlizing agents are, for example, glycol stearic esters, such as ethylene glycol distearate, and also fatty acid monoglycol esters. The dyes which can be used are the substances suitable and approved for cosmetic purposes, as are listed, for example, in the publication "Kosmetische Färbemittel" [Cosmetic Colorants] by the Farbstoffkommission der Deutschen Forschungsgemeinschaft [Dyes Commission of the German Research Society], Verlag Chemie, Weinheim, 1984, pp. 81–106.

The total amount of auxiliaries and additives can be from 1 to 10% by weight, preferably from 2 to 5% by weight, based on the composition.

The compositions can be prepared in a manner known per se, i.e. for example by hot, hot-hot/cold or PIT emulsification.

The examples below serve to illustrate the possible applications of the thickeners according to the invention in more detail, without limiting them thereto. The percentages are percentages by weight in all cases.

Example 1

O/W Cream

A

Hostacerin DGI (Clariant GmbH) 2.00%

Mineral oil, low viscosity 8.00%

Isopropyl palmitate 4.00%

Eutanol G (Henkel) 4.00%

B

Copolymer (Clariant GmbH) 1.20%

C

Hostapon KCG (Clariant GmbH) 0.80%

Water ad 100%

Preservative q.s.

D

Fragrances 0.40%

Preparation Procedure

I Stir B into A, then add C and stir well

II Stir D into I

III Homogenize

Example 2

O/W Skin Milk

A

Hostacerin DGMS (Clariant GmbH) 2.00%

Mineral oil, high viscosity 8.00%

Isopropyl palmitate 5.00%

Cetiol 868 (Henkel) 4.00%

B

Copolymer 0.50%

C

Hostapon KCG (Clariant GmbH) 2.00%

Glycerol 4.00%

Water ad 100%

Preservative q.s.

D

Fragrances 0.30%

Preparation Procedure

I Melt A to about 70° C.; add B

II Heat C to about 70° C.

III Stir II into I and stir until cool

IV Add D at about 35° C.

V Homogenize

Example 3

O/W Skin Milk

A

Hostacerin DGL (Clariant GmbH) 2.00%

Isopropyl palmitate 4.00%

Almond oil 5.00%

Wheatgerm oil 1.00%

Cetiol SN (Henkel) 8.00%

B

Copolymer 0.60%

C

Water ad 100%

Preservatives q.s.

D

Fragrances 0.30%

Preparation Procedure

I Mix A and B and stir into C

II Add D

III Homogenize

Example 4

O/W Skin Milk

A

Hostaphat CG 120 (Clariant GmbH) 1.50%

Mineral oil, low viscosity 5.00%

Miglyol 812 (Dynamit Nobel) 4.00%

Isopropyl palmitate 6.00%

Soya oil 3.00%

Jojoba oil 2.00%

B

Copolymer 0.80%

C

Hostapon KCG (Clariant GmbH) 1.00%

Water ad 100%

Glycerol 3.00%

Soda (10% in water) 1.20%

Preservatives q.s.

D

Fragrances 0.30%

Preparation Procedure

I Stir B into A, add C and mix well

II Add D

III Homogenize

Commercial Products

®Hostacerin DGI (Clariant GmbH) polyglyceryl-2 sesquiisostearate

®Eutanol G (Henkel) octyldodecanol

Copolymer copolymer as in Example 1

®Hostapon KCG (Clariant GmbH) sodium cocoyl glutamate

Hostacerin DGMS (Clariant GmbH) polyglyceryl-2 stearate

®Cetiol 868 (Henkel) octyl stearate

Hostacerin DGL (Clariant GmbH) polyglyceryl-2 PEG-10 laurate

®Cetiol SN (Henkel) cetearyl isononanoate

®Hostaphat CG 120 (Clariant GmbH) octyldecyl phosphate

®Miglyol 812 (Dynamit Nobel) capryl triglyceride

We claim:

1. A process for thickening a fluid comprising combining the fluid with a water-soluble or water-swellable polymer which, in addition to from 0.01 to 5% by weight of crosslinking structures originating from monomers having at least two olefinic double bonds, comprises, in random distribution, from 1 to 50% by weight of the repeat structural unit of the formula (1) and from 49.99 to 98.99% by weight of the repeat structural unit of the formula (2),

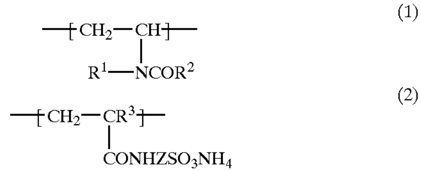

in which $R^1$, $R^2$ and $R^3$ independently of one another are a hydrogen atom or a methyl group, and Z is a $C_1$–$C_4$-alkylene group.

2. The process of claim 1 wherein the fluid comprises a pharmaceutical preparation or a cosmetic preparation.

3. The process of claim 1 wherein the fluid comprises from 0.1 to 5 weight percent of the water-soluble or water-swellable polymer.

4. The process of claim 1 wherein the fluid comprises a pH of 2.5 to 7.

5. The process of claim 1 wherein the fluid comprises from 0.5 to 2 weight percent of the water-soluble or water-swellable polymer.

6. The process of claim 1 wherein the fluid comprises from 0.7 to 1 weight percent of the water-soluble or water-swellable polymer.

7. The process of claim 1 wherein the fluid comprises a pH of from 3.0 to 5.0.

* * * * *